United States Patent
Choi et al.

(10) Patent No.: US 6,909,476 B2
(45) Date of Patent: Jun. 21, 2005

(54) COLOR POLYMER DISPERSED LIQUID CRYSTAL DISPLAY AND METHOD FOR MANUFACTURE THEREOF

(75) Inventors: Soo Young Choi, Ulsan (KR); Sang Un Choi, Kyoungki-do (KR); Hoan Su Shim, Kyoungki-do (KR); Sung Woon Kim, Kyoungki-do (KR)

(73) Assignee: BOE-HYDIS Technology Co., Ltd., Kyoungki-do (KR)

( * ) Notice: Subject to any disclaimer, the term of this patent is extended or adjusted under 35 U.S.C. 154(b) by 89 days.

(21) Appl. No.: 10/621,541

(22) Filed: Jul. 17, 2003

(65) Prior Publication Data

US 2004/0189893 A1 Sep. 30, 2004

(30) Foreign Application Priority Data

Mar. 31, 2003 (KR) ................. 10-2003-0019941

(51) Int. Cl.⁷ ............................................. G02F 1/1333
(52) U.S. Cl. .......................................... 349/86; 349/183
(58) Field of Search ................... 349/86, 183

(56) References Cited

U.S. PATENT DOCUMENTS 4,662,720 A * 5/1987 Fergason ................... 349/105
5,223,959 A * 6/1993 Wu et al. .................... 349/36

FOREIGN PATENT DOCUMENTS

JP 03186815 A * 8/1991 ................ 349/165

* cited by examiner

Primary Examiner—Kenneth Parker
Assistant Examiner—Thanh-Nhan P Nguyen
(74) Attorney, Agent, or Firm—Ladas & Parry LLP

(57) ABSTRACT

A color polymer dispersed liquid crystal display includes a lower substrate, an upper substrate, color liquid crystal-polymer films, and two transparent liquid crystal driving electrodes, among others. The color liquid crystal-polymer films are formed by foaming polymer films mixed with red, green and blue pigments to form porous films of red, green, and blue colors and then dropping and injecting liquid crystal into droplets of the porous films under vacuum condition. One of the two transparent liquid crystal driving electrodes is disposed between the lower substrate and the PDLC films, and the other is disposed between the PDLC films and the upper substrate. The changes in properties of the PDLC films, which may be caused by unstable phase separation in a conventional phase separation process, are reduced, and the colors are improved.

13 Claims, 4 Drawing Sheets

COLOR POLYMER DISPERSED LIQUID CRYSTAL DISPLAY AND METHOD FOR MANUFACTURE THEREOF

BACKGROUND OF THE INVENTION

1. Field of the Invention

The present invention relates to a polymer dispersed liquid crystal display, and more particularly to a color polymer dispersed liquid crystal display, which reduces changes in properties caused by unstable phase separation and produces improved colors, and a method for manufacturing the same.

2. Description of the Prior Art

A polymer dispersed liquid crystal display ("PDLCD") has a structure wherein a PDLC film consisting of liquid crystal droplets, which have a diameter of 1 to 2 μm and are dispersed in a polymer film, instead of a conventional liquid crystal film consisting only of liquid crystal molecules, is disposed between a pair of transparent substrates. The PDLCD requires no polarizer and can be easily manufactured due to its flexibility. Applications of the PDLCD with improved brightness include widescreen display devices and light-modulating window projection TVs.

If an electric field is applied to a PDLC film inserted between a pair of driving electrodes, a director of the liquid crystal will be oriented in the direction of the electric field. When the ordinary refractive index $n_o$ of the liquid crystal is equal to the refractive index $n_p$ of the polymer, the PDLC film becomes transparent by light penetration, thereby making the PDLCD appear white. When the electric field is removed, the director of the liquid crystal returns to its initially chaotic state due to the surface anchoring energy. At this time, the effective refractive index of the liquid crystal greatly deviates from the refractive index np of the polymer. The difference in refractive indexes causes interfacial light scattering, whereby the PDLC film becomes opaque and the PDLCD appears black.

As methods for dispersing liquid crystal droplets in a polymer, phase separation and emulsification are available. The phase separation is based on a principle that phase separation of an initially homogeneous liquid crystal-polymer (or precursor) mixture is achieved by polymerization, cooling or solvent evaporation. The emulsification is based on a principle that the liquid crystal in an initially heterogeneous liquid crystal-polymer aqueous solution is encapsulated by the polymer during evaporation of water. PDLC films are typically formed by phase separation.

However, when a PDLC film is formed by phase separation, it is difficult and practically impossible to achieve a complete phase separation, because an initially homogeneous phase becomes heterogeneous during phase separation by various methods. Accordingly, a PDLC film obtained by phase separation may show properties slightly different from its original properties, because the liquid crystal and the polymer (or precursor) contaminate each other. Particularly, the properties of the PDLC film are affected by minor changes in processing conditions.

Also, a color PDLC film can be formed by a guest-host method or holography. However, these methods enable only single color reflective displays. In the prior art, full color reflective displays have been achieved by combining PDLC films to form a multilayer structure. Such a stacking structure, however, has a problem in the link between layers and increases the driving voltage and the cost of manufacture.

Although a color PDLCD can be prepared using an existing color filter, UV light cannot penetrate into the color filter. Accordingly, the polymerization induced phase separation (PIPS) utilizing UV polymerization, which is the most generally used method to prepare a PDLCD, cannot be used to prepare a color PDLCD.

A color PDLCD can also be made by a color sequential display method. However, this method has technical drawbacks because it requires high-speed responsiveness.

Korean Patent Application No. 10-1999-0016162 discloses a PDLCD which enables a full-color display by a polymer film formed by mixing a polymeric material with a liquid crystal and dichroic dyes for producing particular colors. According to the disclosure of this reference, liquid crystal cells of a color PDLCD can be formed by the following two methods.

The first method forms liquid crystal cells by coating a polymer film, which contains a mixed solution of a liquid crystal and dyes, and forming polymer domains of red, green and blue colors.

According to the second method, a polymer film is coated and cured to have a plurality of pores linked to each another. A mixture of dyes and a liquid crystal is injected into the exposed pores of the cured polymer film to form liquid crystal cells. It is also possible to form the liquid crystal cells by ink-jetting a mixture of a liquid crystal and red, green and blue dyes onto a predetermined position of the cured polymer film.

The first method forms fine pores and pattern by curing a photoreactive material. As is generally known, however, it is difficult to achieve high resolution by this method. Further, the properties of the liquid crystal are affected during developing process.

Since the second method forms pores linked to each another, colors are likely to be mixed when a mixture of the liquid crystal and the dyes are injected or inkjetted. Further, although the fine pores are linked to each another, it is difficult to completely inject the liquid crystal into the polymer simply by inkjetting the mixture.

The prior art mentioned above uses dyes for producing colors. However, dyes cannot produce a full range of colors and are less reliable, when compared to pigments used in existing color filters. Particularly, dyes used in form of a mixture with a liquid crystal may deteriorate the properties of the liquid crystal.

SUMMARY OF THE INVENTION

Accordingly, the present invention has been made to solve the above-mentioned problems occurring in the prior art, and one object of the present invention is to provide a color PDLCD, which prevents any change in properties of a PDLC film caused by incomplete phase separation, and a method for manufacturing the same.

Another object of the present invention is to provide a color PDLCD which produces improved colors and a method for manufacturing the same.

In order to accomplish the above objects, there is provided a color PDLCD comprising: a lower substrate; an upper substrate formed on the lower substrate with a predetermined space therebetween; color PDLC films formed by foaming polymer films mixed respectively with red, green and blue pigments to form porous films of red, green and blue colors and then dropping and injecting a liquid crystal into droplets of the porous films under vacuum condition; and two transparent liquid crystal driving electrodes, one disposed between the lower substrate and the PDLC films and the other disposed between the PDLC films and the upper substrate.

The lower and upper substrates can be made of a glass substrate or a plastic film. The upper substrate can also be made of an organic film.

The porous films have a thickness of 1 to 30 μm.

The PDLCD of the present invention further comprises barriers in a stripe pattern on the lower substrate in order to divide colors. Preferably, the barriers have a height of 1 to 30 μm.

In order to accomplish the above objects of the present invention, there is also provided a method for manufacturing a color PDLCD, comprising the steps of: forming pixel electrodes on a lower substrate; forming polymer films mixed respectively with red, green and blue pigments on the lower substrate including the pixel electrodes; forming porous films of red, green and blue colors by foaming the polymer films; forming color PDLC films by dropping and injecting a liquid crystal into droplets of the porous films under vacuum condition; and combining an upper substrate having a common electrode on the inside surface thereof with the lower substrate including the color PDLC films.

The method for manufacturing a color PDLCD further comprises a step of forming barriers for dividing colors after forming the pixel electrodes and before forming the polymer films mixed with pigments.

The polymer films are formed by mixing a transparent polymeric material, such as acryl, styrene or carbonate, with red, green and blue pigments using a screen pattern printing or inkjet injecting method.

The polymer films are foamed by mechanical stirring, using a reaction generating gas or a foaming agent, by removing a soluble material or by spraying.

The upper substrate can be made by sequentially forming a transparent electrode and an organic film after applying a protective film on the PDLC films. The organic film is formed by a spin coating or printing method.

According to the present invention, the PDLC films are prepared by foaming polymer films mixed with red, green and blue pigments to form porous films and then dropping and injecting a liquid crystal into the porous films under vacuum condition. Therefore, it is possible to reduce changes in properties of the PDLC films, which may be caused by unstable phase separation in a conventional phase separation process. In addition, the present invention using pigments can produce further improved colors.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
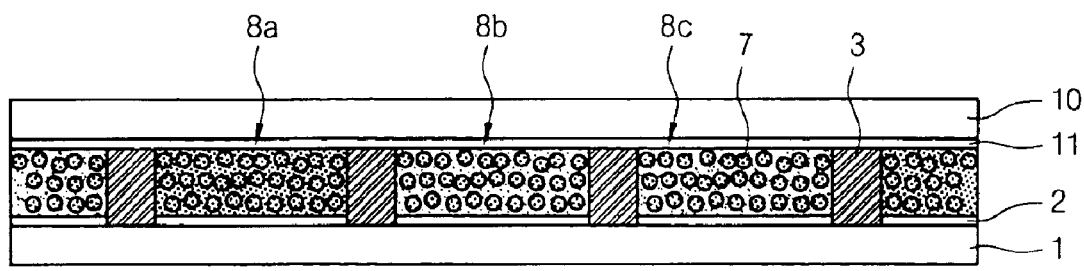
FIG. 1 is a cross-sectional view of a color polymer dispersed liquid crystal display according to the present invention.

Hereinafter, a preferred embodiment of the present invention will be described with reference to the accompanying drawings. In the following description and drawings, the same reference numerals are used to designate the same or similar components, and so repetition of the description on the same or similar components will be omitted.

FIG. 1 is a cross-sectional view of a color PDLCD according to the present invention.

As shown in FIG. 1, the color PDLCD according to the present invention has a structure wherein a lower substrate 1 and an upper substrate 10 respectively including a pixel electrode 2 and a common electrode 11, which are transparent liquid crystal driving electrodes, are adhered to each other with red, green and blue PDLC films 8a, 8b and 8c disposed therebetween.

Also, barriers 3 for dividing colors are formed at the boundaries of the red, green and blue PDLC films 8a, 8b and 8c. It is, however, possible to achieve the present invention without forming the barriers 3.

The PDLC films 8a, 8b and 8c are prepared by foaming polymer films mixed respectively with red, green and blue pigments to form red, green and blue porous films and then dropping and injecting a liquid crystal into droplets of the porous films under vacuum condition, without using a conventional phase separation method. The polymer films are formed by mixing each color pigment with a transparent polymeric material at an appropriate ratio to be dispersed in the polymeric material.

The two substrates 1 and 10 can be made of a glass substrate or a plastic film. Particularly, the upper substrate can be replaced by an organic film.

The PDLCD of the present invention is manufactured through the following steps. FIGS. 2a to 2f are cross-sectional views for explaining a process for manufacturing the PDLCD.

Figure 2A:
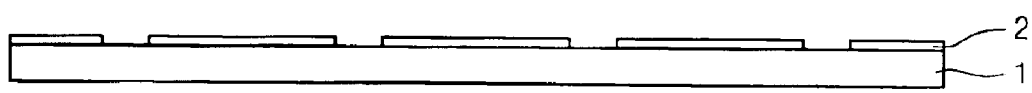
FIGS. 2a to 2f are cross-sectional views for explaining a process of manufacturing a color polymer dispersed liquid crystal display according to the present invention.

Referring to FIG. 2a, a transparent metal film, such as indium tin oxide (ITO), is deposited on the lower substrate 1 made of a transparent substrate, such as a glass substrate or a plastic film, and patterned to form pixel electrodes 2.

Figure 2B:
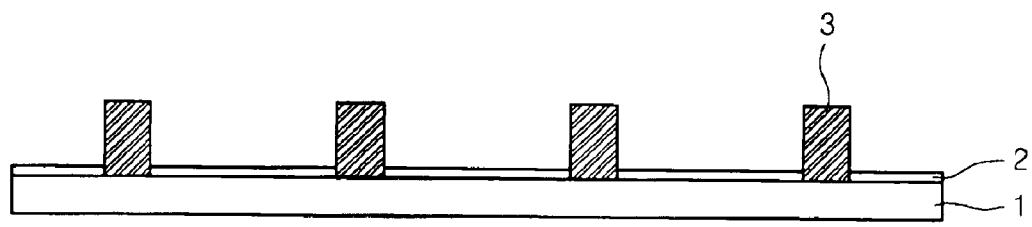

Referring to FIG. 2b, the barriers 3 are provided in a stripe pattern at the boundaries between neighboring pixel electrodes 2. The barriers 3 are formed by a screen pattern printing or photolithographic process. A photosensitive material or a polymeric material capable of being printed is used to form the barriers. Each barrier has a height corresponding to the cell gap of the PDLCD, for example, 1 to 30 μm.

It is, however, possible to achieve the present invention without forming the barriers 3.

Figure 2C:
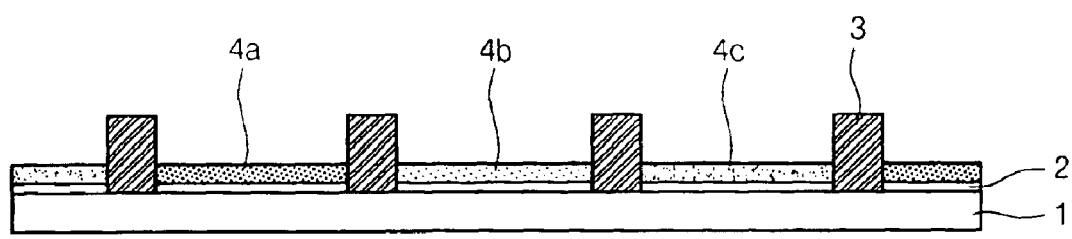

Referring to FIG. 2c, color polymer films 4a, 4b and 4c, which include red, green and blue pigments, respectively, are formed on the lower substrate 1 including the pixel electrodes 2. In order to form the color polymer films 4a, 4b and 4c, an inkjet injecting method, instead of the screen pattern printing, can be used. Dyes as well as pigments can be used as a coloring material, although dyes has inferior color producibility.

The polymer films 4a, 4b and 4c are prepared by mixing pigments with a transparent polymeric material at an appropriate ratio to be dispersed in the polymeric material. The transparent polymeric material includes a general transparent plastic material, such as acryl, styrene or carbonate. Particularly, when using a transparent polymer having a refractive index equal or similar to the ordinary refractive index $n_o$ of the liquid crystal, it is possible to manufacture a PDLCD with further improved transmissivity.

Figure 2D:
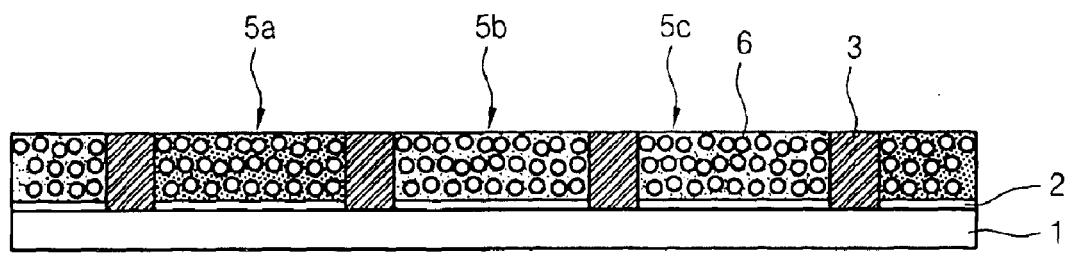

Referring to FIG. 2d, stripe-shaped porous films 5a, 5b and 5c of red, green and blue colors are formed by foaming the polymer films of red, green and blue colors. The polymer films can be foamed by a variety of methods, such as mechanical stirring, use of a reaction generating gas or a foaming agent, removal of a soluble material, or spraying. As a foaming agent, a volatile foaming agent or a dissoluble forming agent can be used. The drawing reference numeral "6" represents droplets in the porous films.

Figure 2E:
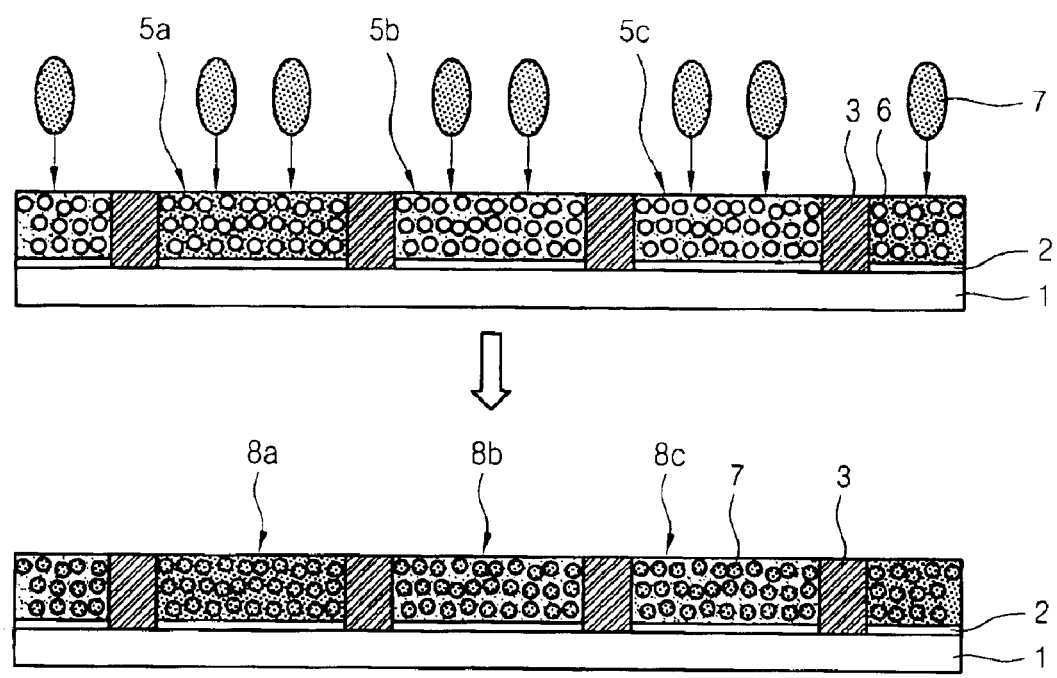

Referring to FIG. 2e, a suitable amount of a liquid crystal 7 is dropped onto the porous films 5a, 5b and 5c under vacuum condition to be vacuum-injected into the droplets 6 of the porous films 5a, 5b and 5c and to thereby form the PDLC films 8a, 8b and 8c of red, green and blue colors.

Figure 2F:
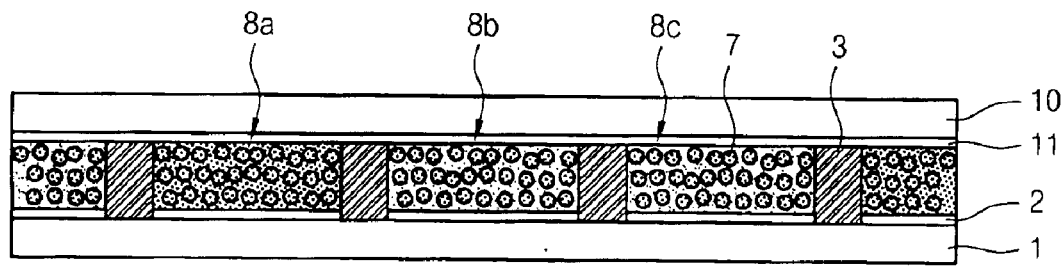

Referring to FIG. 2f, the upper substrate 10 having the common electrode 11 made of a transparent metal film, such as ITO, is adhered to the upper surface of the lower substrate 1 having the PDLC films 8a, 8b and 8c of red, green and blue colors thereon. As a result, the color PDLCD of the present invention is completed.

Like the lower substrate 1, the upper substrate 10 is made of a transparent substrate, such as a glass substrate or a plastic film. Also, the upper substrate 10 can be replaced by the PDLC films 8a, 8b and 8c coated with a protective film, on which a transparent electrode and an organic film are sequentially formed. An organic film can be formed by spin coating or printing.

As described above, the PDLCD prepared by the present invention has the following advantages.

Since the PDLC films are formed by foaming polymer films to form porous films and then dropping and injecting a liquid crystal in the porous films, they can prevent contamination of the liquid crystal or the polymer as occurred in the conventional phase separation and exhibit improved optical properties. Further, since the liquid crystal is injected after preparation of the porous films, it is possible to prevent any structural change which may be caused by a minor change in processing conditions during the conventional phase separation.

Since the PDLC films are obtained from a polymeric material mixed with pigments, they have a reduced rate of liquid crystal contamination, as compared to a mixture of a liquid crystal and dyes. Also, the PDLC films can maintain original properties of the liquid crystal.

As described above, the PDLC films are formed by patterning and foaming a polymeric material mixed with pigments to form porous films and then injecting a liquid crystal into the porous films. Therefore, it is easy to select a polymeric material suitable for a liquid crystal, when compared to a method of forming fine pores and pattern by curing a photoreactive material as disclosed in the prior art reference mentioned above. It is also possible to prevent colors from being mixed through the linked fine pores, which is a drawback of the prior art mentioned above, by injecting a liquid crystal after forming porous films by patterning and foaming a polymeric material mixed with pigments.

In the prior art, the amount of dyes which are mixed with a liquid crystal should be adjusted to control the colors. Although there is a limitation in adjusting the amount of dyes mixed with a liquid crystal, the amount of pigments mixed with a polymeric material can be easily adjusted. Therefore, the present invention can easily control the colors.

In addition, the present invention can effectively inject a liquid crystal by dropping it under vacuum condition.

As stated above, the present invention prepares the PDLC films by foaming polymer films mixed with red, green and blue pigments to form porous films and then dropping and injecting a liquid crystal into the porous films under vacuum condition. Therefore, it is possible to reduce changes in properties of the PDLC films which may be caused by unstable phase separation in a conventional phase separation process. In addition, the present invention using pigments can produce further improved colors.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A color polymer dispersed liquid crystal display comprising:
   a lower substrate;
   an upper substrate formed on the lower substrate with a predetermined space therebetween;
   color liquid crystal-polymer films formed by foaming polymer films mixed respectively with red, green and blue pigments to form porous films of red, green and blue colors and then dropping and injecting a liquid crystal into droplets of the porous films under vacuum condition; and
   two transparent liquid crystal driving electrodes, one disposed between the lower substrate and the PDLC films and the other disposed between the PDLC films and the upper substrate.

2. The color polymer dispersed liquid crystal display according to claim 1, wherein said lower and upper substrates are made of a glass substrate or a plastic film.

3. The color polymer dispersed liquid crystal display according to claim 1, wherein said upper substrate is made of an organic film.

4. The color polymer dispersed liquid crystal display according to claim 1, wherein said porous films have a thickness of 1 to 30 $\mu$m.

5. The color polymer dispersed liquid crystal display according to claim 1, further comprising barriers in a stripe pattern on said lower substrate in order to divide colors.

6. The color polymer dispersed liquid crystal display according to claim 5, wherein said barriers have a height of 1 to 30 $\mu$m.

7. A method for manufacturing a color polymer dispersed liquid crystal display, comprising the steps of:
   forming pixel electrodes on a lower substrate;
   forming polymer films mixed respectively with red, green and blue pigments on the lower substrate including the pixel electrodes;
   forming porous films of red, green and blue colors by foaming the polymer films;
   forming color liquid crystal-polymer films by dropping and injecting a liquid crystal into droplets of the porous films under vacuum condition; and
   combining an upper substrate having a common electrode on the inside surface thereof with the lower substrate including the color liquid crystal-polymer films.

8. The method according to claim 7, further comprising a step of forming barriers for dividing colors after forming the pixel electrodes and before forming the polymer films mixed with pigments.

9. The method according to claim 7, wherein said polymer films are formed by a screen pattern printing or inkjet injecting method.

10. The method according to claim 7, wherein said polymer films are formed by mixing a transparent polymeric material selected from a group consisting of acryl, styrene and carbonate with pigments.

11. The method according to claim 7, wherein said polymer films are foamed by a method selected from mechanical stirring, use of a reaction generating gas or a foaming agent, removal of a soluble material and spraying.

12. The method according to claim 7, wherein said upper substrate is made by sequentially forming a transparent electrode and an organic film after applying a protective film on said liquid crystal-polymer films.

13. The method according to claim 12, wherein said organic film is formed by a spin coating or printing method.

* * * * *